(12) United States Patent
Tsubota et al.

(10) Patent No.: US 8,319,189 B2
(45) Date of Patent: Nov. 27, 2012

(54) RADIOGRAPHIC IMAGING ASSISTANCE DEVICE, RADIOGRAPHIC IMAGING DEVICE AND STORAGE MEDIUM STORING A PROGRAM

(75) Inventors: Keiji Tsubota, Kanagawa (JP); Yutaka Yoshida, Kanagawa (JP); Takeshi Kamiya, Kanagawa (JP); Naoyuki Nishino, Kanagawa (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 764 days.

(21) Appl. No.: 12/546,712

(22) Filed: Aug. 25, 2009

(65) Prior Publication Data

US 2010/0054416 A1 Mar. 4, 2010

(30) Foreign Application Priority Data

Aug. 28, 2008 (JP) .................................. 2008-220113
Jul. 30, 2009 (JP) .................................. 2009-178049

(51) Int. Cl.
*H01L 27/146* (2006.01)
*H05G 1/64* (2006.01)
(52) U.S. Cl. ..................................... 250/370.09; 378/98
(58) Field of Classification Search ............. 250/370.09, 250/370.08, 362, 366; 378/98
See application file for complete search history.

(56) References Cited

U.S. PATENT DOCUMENTS

2009/0279772 A1* 11/2009 Sun et al. ....................... 382/141

FOREIGN PATENT DOCUMENTS

| JP | 2002-336225 A | 11/2002 |
|----|---------------|---------|
| JP | 2005-095635 A | 4/2005 |
| JP | 2008-099808 A | 5/2008 |

* cited by examiner

*Primary Examiner* — David Porta
*Assistant Examiner* — Faye Boosalis
(74) *Attorney, Agent, or Firm* — SOLARIS Intellectual Property Group, PLLC

(57) ABSTRACT

A radiographic imaging assistance device is provided. An acquisition component acquires position information representing positions of defective pixels of an imaging device, the imaging device being plurally provided with pixels comprising detection elements which detect radiation that has passed through a subject of imaging, and the imaging device carrying out imaging by generating image information which represents a radiographic image in accordance with radiation amounts detected by the detection elements and storing the image information in a pre-specified storage region. A judgment component, based on detection region information, which represents a detection region with a size corresponding to the subject of imaging, and the acquired position information, judges whether or not an influence from the defective pixels in a detection region that is represented by the detection region information is within an acceptable level that accepts imaging a radiographic image.

16 Claims, 15 Drawing Sheets

PATIENT: YAMADA, HANAKO

ETHNICITY: JAPANESE

GENDER: FEMALE

AGE: 15

IMAGING POSITIONS: A, B, C, D, E

DETECTION REGION

DETECTION-CAPABLE REGION

DETECTION REGION

DETECTION-CAPABLE REGION

RADIOGRAPHIC IMAGING ASSISTANCE DEVICE, RADIOGRAPHIC IMAGING DEVICE AND STORAGE MEDIUM STORING A PROGRAM

CROSS-REFERENCE TO RELATED APPLICATION

This application claims priority under 35 USC 119 from Japanese Patent Applications No. 2008-220113 filed on Aug. 28, 2008 and No. 2009-178049 filed on Jul. 30, 2009, the disclosures of which are incorporated by reference herein.

BACKGROUND OF THE INVENTION

1. Field of the Invention

The present invention relates to a radiographic imaging assistance device, a radiographic imaging device, and a storage medium storing a program.

2. Description of the Related Art

In recent years, FPDs (flat panel detectors) have been realized in which a radiation-sensitive layer is disposed on a TFT (thin film transistor) active matrix substrate and radiation can be directly converted to digital data. Using these FPDs and the like, radiographic image detection devices (below referred to as electronic cassettes) have been realized which carry out imaging by generating image information, which represents a radiographic image corresponding to amounts of irradiated radiation, and storing the generated image information.

However, this kind of electronic cassette has a problem in that, because defective pixels of an FPD increase in number over time, irregularities arise in the radiographic images that are obtained by imaging.

Japanese Patent Application Laid-Open (JP-A) No. 2002-336225 has disclosed a technology of storing a correction image for correcting sensitivities of individual pixels of an electronic cassette in advance, and using this correction image to correct image irregularities caused by defective pixels.

Meanwhile, JP-A No. 2008-99808 has disclosed a technology of administering and updating quality conditions of plural electronic cassettes, and selecting the most suitable electronic cassettes for imaging.

However, the technology of JP-A No. 2002-336225 cannot correct image irregularities caused by defective pixels that arise over time. Therefore, as the defective pixels increase in number, the quality of radiographic images falls and it is not possible to obtain radiographic images of the fundamentally required quality. In such cases, it is necessary to redo the imaging and subjects of imaging are purposelessly exposed to radiation, and this is a problem.

In the technology of JP-A No. 2008-99808, the electronic cassettes are selected without regard to positions of defective pixels. Therefore, there are cases in which, depending on the positions of defective pixels, it is not possible to obtain radiographic images of the fundamentally required quality. In such cases, it is necessary to redo the imaging and subjects of imaging are purposelessly exposed to radiation, and this is a problem.

SUMMARY OF THE INVENTION

The present invention has been made in order to solve the problems described above, and an object is to provide a radiographic imaging assistance device, a radiographic imaging device and a storage medium storing a program that are capable of avoiding repetitions of imaging due to defective pixels.

According to the first aspect of the invention, there is provided a radiographic imaging assistance device comprising: an acquisition component that acquires position information representing positions of defective pixels of an imaging device, the imaging device being plurally provided with pixels comprising detection elements which detect radiation that has passed through a subject of imaging, and the imaging device carrying out imaging by generating image information which represents a radiographic image in accordance with radiation amounts detected by the detection elements and storing the image information in a pre-specified storage region; a judgment component that, on the basis of detection region information, which represents a detection region with a size corresponding to the subject of imaging, and the position information acquired by the acquisition component, judges whether or not an influence from the defective pixels in a detection region that is represented by the detection region information is within an acceptable level that accepts imaging a radiographic image; and a control component that performs control such that information based on a judgment result judged by the judgment component is displayed at a display component or notified to an external device.

According to the second aspect of the invention, there is provided a radiographic imaging device comprising: an imaging component that is plurally provided with pixels comprising detection elements which detect radiation which has passed through a subject of imaging, and that carries out imaging by generating image information which represents a radiographic image in accordance with radiation amounts detected by the detection elements and storing the image information in a pre-specified storage region; an acquisition component that acquires position information representing positions of defective pixels of the imaging component; a judgment component that, on the basis of detection region information, which represents a detection region with a size corresponding to the subject of imaging, and the position information acquired by the acquisition component, judges whether or not an influence from the defective pixels in a detection region that is represented by the detection region information is within an acceptable level that accepts imaging a radiographic image; and a control component that performs control such that information based on a judgment result judged by the judgment component is displayed at a display component or notified to an external device.

According to the third aspect of the invention, there is provided a storage medium readable by a computer. The storage medium storing a program of instructions executable by the computer to perform a function for assisting radiographic imaging. The function includes: (a) acquiring position information representing positions of defective pixels of an imaging device, the imaging device being plurally provided with pixels comprising detection elements which detect radiation that has passed through a subject of imaging, and the imaging device carrying out imaging by generating image information which represents a radiographic image in accordance with radiation amounts detected by the detection elements and storing the image information in a pre-specified storage region; (b) on the basis of detection region information, which represents a detection region with a size corresponding to the subject of imaging, and the position information acquired in (a), judging whether or not an influence from the defective pixels in a detection region that is represented by the detection region information is within an acceptable level that accepts imaging a radiographic image; and (c) performing control such that information based on a judgment result judged in (b) is displayed at a display component or notified to an external device.

BRIEF DESCRIPTION OF THE DRAWINGS

FIG. 7 is a view illustrating an example of a display screen relating to the first exemplary embodiment, at which patient information and information on a subject of imaging are displayed.

DETAILED DESCRIPTION OF THE INVENTION

[First Exemplary Embodiment]

Herebelow, the best exemplary embodiment for carrying out the present invention will be described in detail with reference to the drawings.

Figure 1:
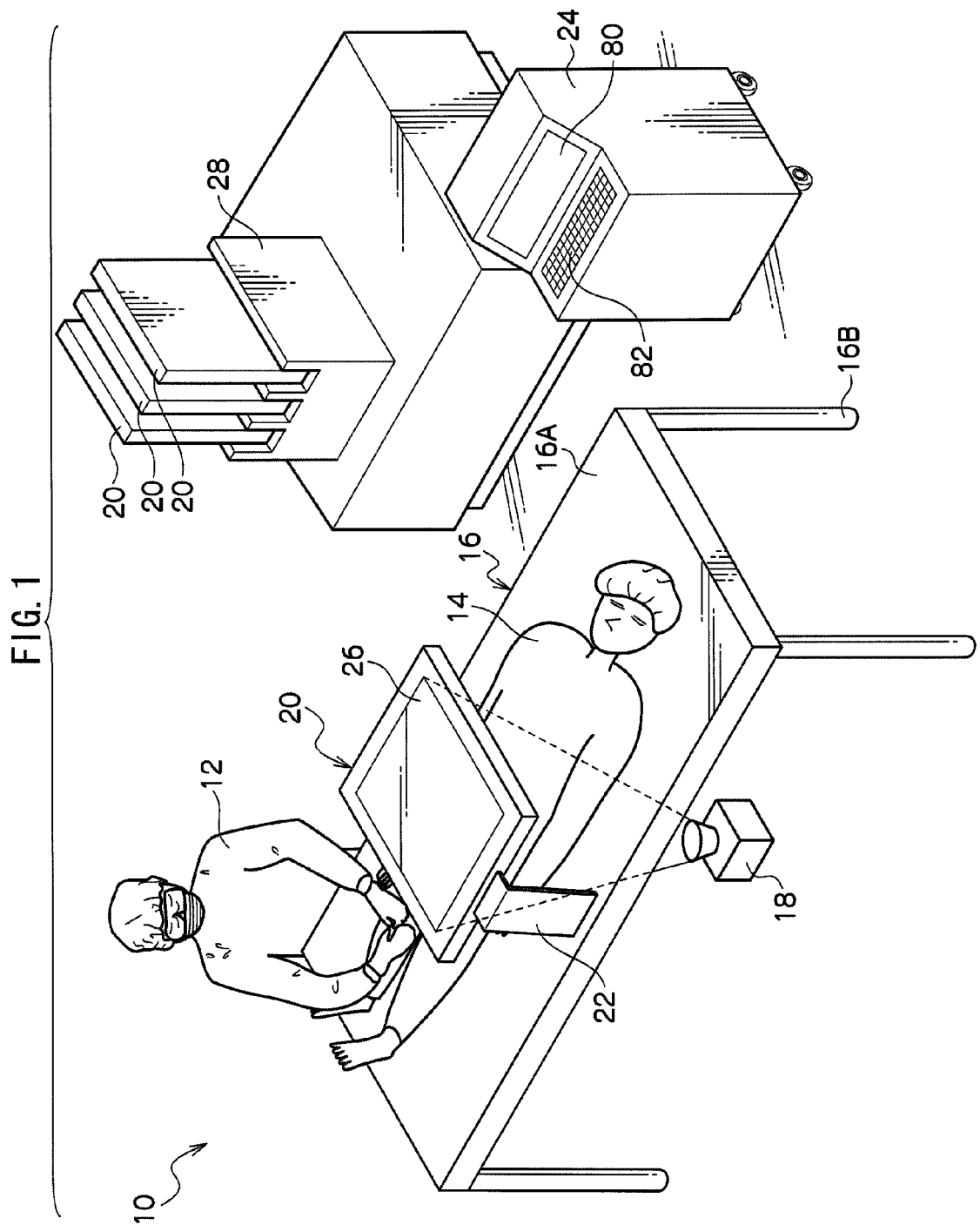
FIG. 1 is a view illustrating conditions in an operating room in which an imaging system relating to a first exemplary embodiment is disposed.

Firstly, the constitution of a radiographic imaging system 10 relating to the present exemplary embodiment (referred to as the imaging system 10 hereafter) will be described. FIG. 1 illustrates a state in which the imaging system 10 is disposed in an operating room, as an example of conditions in which the imaging system 10 relating to the present exemplary embodiment will be disposed.

The imaging system 10 carries out imaging of a radiographic image in accordance with operations by a doctor 12 or a radiographer or the like. The imaging system 10 is provided with a bed 16, on which a patient 14 is rested, a radiation irradiation device 18, an electronic cassette 20, a support member 22 and a console 24. The radiation irradiation device 18 irradiates radiation X, constituted with a radiation amount in accordance with imaging a conditions, at the patient 14. The electronic cassette 20 carries out imaging, by detecting the radiation X that has passed through the patient 14, generating radiographic image information (below referred to simply as image information) which represents a radiographic image corresponding to the detected radiation amounts, and storing the image information in a pre-specified storage region. The support member 22 is provided at the bed 16, and is a cantilever support for the electronic cassette 20 to the side of the bed 16 at which the patient 14 is rested. The console 24 controls the radiation irradiation device 18 and the electronic cassette 20.

The bed 16 is constituted with a material that transmits the radiation X, and is provided with a platform 16A and leg portions 16B. The platform 16A is a substantially rectangular flat board on which the patient 14 is rested. The leg portions 16B are provided at the four corners of the platform 16A and support the platform 16A.

The radiation irradiation device 18 is disposed at a rear side of the platform 16A (a side thereof opposite to the side at which the patient 14 is rested), such that the radiation X is irradiated at the patient 14 on the bed 16 from the rear side of the platform 16A.

The electronic cassette 20 is provided with a display 26 at a rear face thereof, which displays an imaged radiographic image. The electronic cassette 20 is disposed at the top side of the platform 16A (the side at which the patient 14 is rested) such that, in a state in which the display 26 is oriented upward, the radiation X irradiated from the radiation irradiation device 18 passes through the platform 16A and the patient 14 and is detected by a radiation detector 36.

The support member 22 is provided at a face of the platform 16A at the side at which the patient 14 is rested. The support member 22 is inflected in a substantial "L" shape, a root end portion of which is fixed to the platform 16A. The electronic cassette 20 is removably mounted at a distal end portion of the support member 22.

An accommodation box 28 is disposed in the operating room. The accommodation box 28 accommodates a plurality of the electronic cassette 20. A technician may select the electronic cassette 20 from the plurality of electronic cassettes 20 in accordance with an object of imaging.

Figure 2:
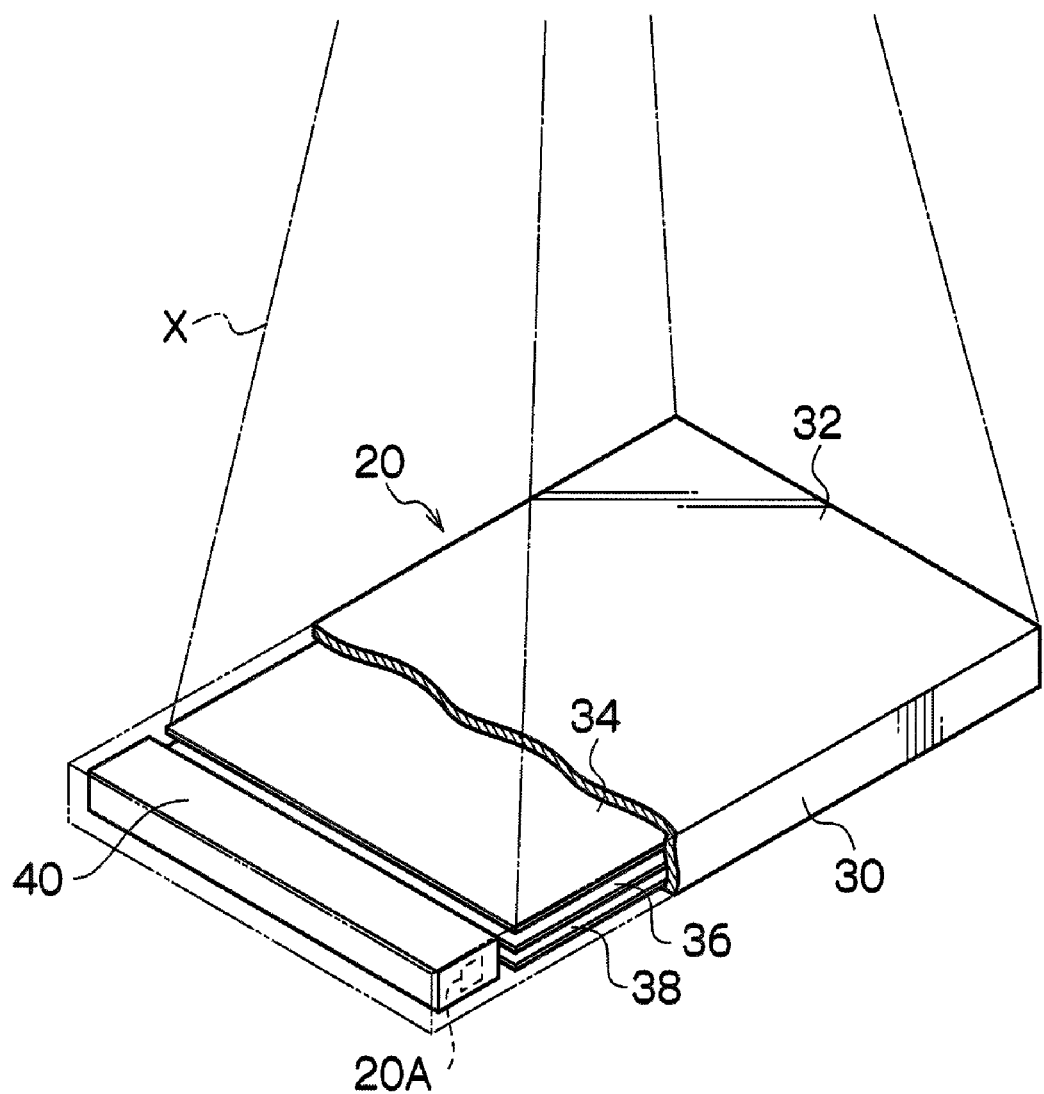
FIG. 2 is a perspective view illustrating internal structure of an electronic cassette relating to the first exemplary embodiment.

FIG. 2 illustrates internal structure of the electronic cassette 20 relating to the present exemplary embodiment.

As shown in FIG. 2, the electronic cassette 20 is provided with a substantially rectangular, flat, plate-form housing 30, which is formed of a material that transmits the radiation X. During use in an operating room or the like, blood and other microorganism contaminants and the like may adhere to the electronic cassette 20. Therefore, the housing 30 is structured to be waterproof and tightly sealed, and is washed with disinfectant as necessary. Thus, an individual electronic cassette 20 may be repeatedly used. A connection terminal 20A, for connection of a communications cable, is provided in a side face of the housing 30. Inside the housing 30, a grid 34, the radiation detector 36 and a lead plate 38 are arranged in this order from the side of an irradiation surface 32 of the housing 30 onto which the radiation X is irradiated. The grid 34 eliminates scattered rays of the radiation X. The radiation detector 36 detects the radiation X that has been irradiated from the irradiation surface 32 and passed through the patient 14, and outputs image information representing a radiographic image in accordance with detected radiation amounts. The lead plate 38 absorbs back-scattered rays of the radiation X.

A case 40 that accommodates electronic circuits, including a microcomputer, and a rechargeable secondary cell is disposed at one end of the interior of the housing 30. The radiation detector 36 and the electronic circuits are operated by electrical power supplied from the secondary cell accommodated in the case 40. In order to prevent the various circuits accommodated inside the case 40 being damaged due to irradiation of the radiation X, it is desirable for a shielding member of lead plating or the like, which shields from radiation, to be disposed at the irradiation surface 32 side of the case 40.

Figure 3:
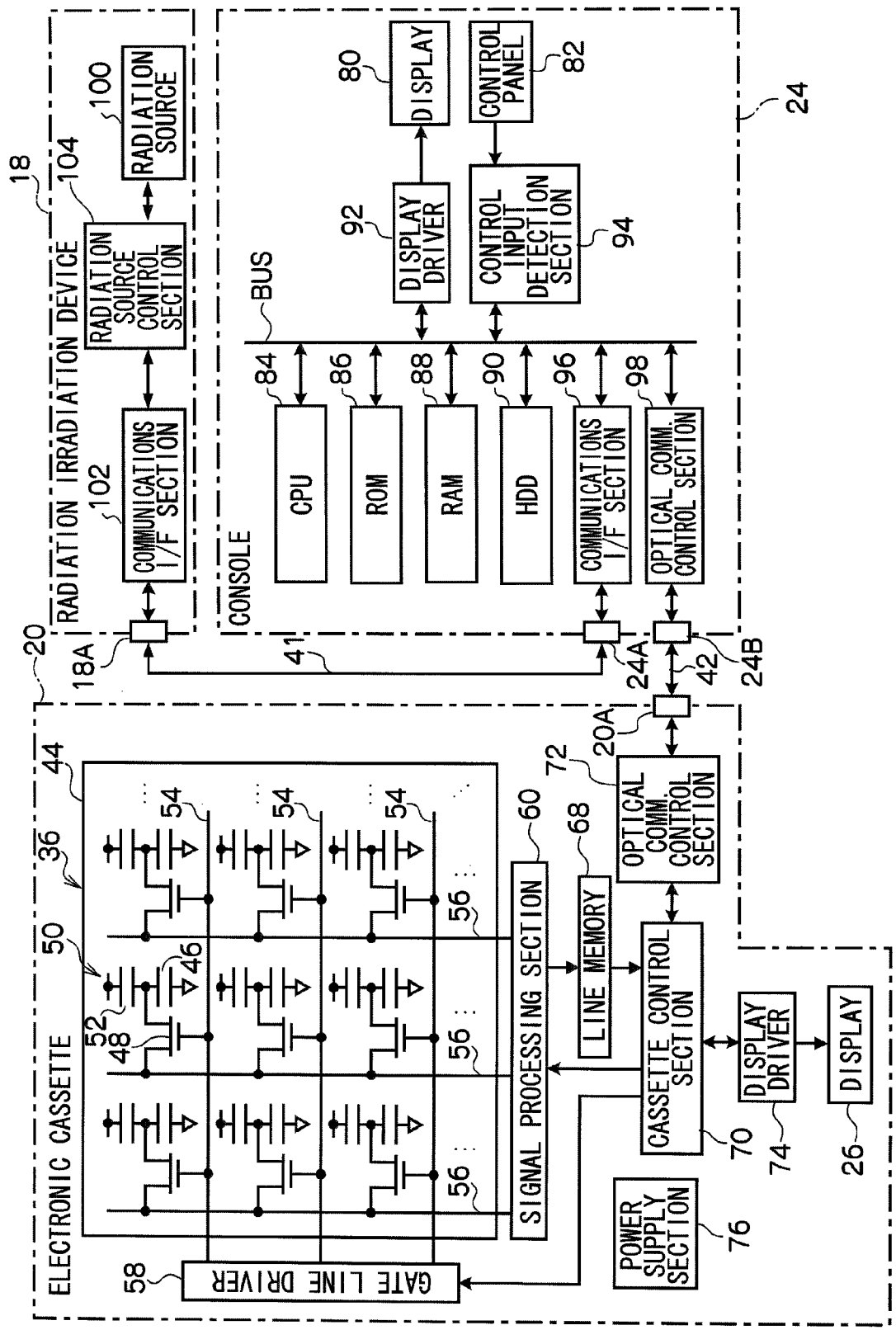
FIG. 3 is a block diagram illustrating structure of the imaging system relating to the first exemplary embodiment.

FIG. 3 shows a block view illustrating structure of the imaging system 10 relating to the present exemplary embodiment.

At the radiation irradiation device 18, a connection terminal 18A for implementing communications with the console 24 is provided. At the console 24, a connection terminal 24A, for implementing communications with the radiation irradiation device 18, and a connection terminal 24B, for implementing communications with the electronic cassette 20, are provided.

The radiation irradiation device 18 is connected to the console 24 via a communications cable 41. At the electronic cassette 20, a communications cable 42 is connected to the connection terminal 20A at times of radiographic imaging, and the electronic cassette 20 is connected to the console 24 via the communications cable 42. In the present exemplary embodiment, in order to enable higher-speed data transfers between the electronic cassette 20 and the console 24, an optical communications cable employing an optical fiber is used for the communications cable 42, and data transfers between the electronic cassette 20 and the console 24 are carried out by optical communications.

The radiation detector 36 incorporated in the electronic cassette 20 is structured by an optoelectronic conversion layer, which absorbs the radiation X and converts the same to electric charges, being layered onto a TFT active matrix substrate 44. The optoelectronic conversion layer is formed of, for example, noncrystalline a-Se (amorphous selenium) of which selenium is a principal component (for example, a proportional content of at least 50%). When the radiation X is irradiated thereon, the optoelectronic conversion layer generates electric charges (electron-hole pairs) thereinside with charge amounts corresponding to irradiated radiation amounts. Thus, the irradiated radiation X is converted to electric charges. Here, instead of a radiation-to-charge conversion material that converts the radiation X directly to electric charges such as amorphous selenium, the radiation detector 36 may indirectly convert to electric charges using a fluorescent material and optoelectronic conversion elements (photodiodes). As fluorescent materials, gadolinium sulfate (GOS), cesium iodide (CsI) and the like are well known. In such a case, a radiation X-to-light conversion is performed by the fluorescent material, and a light-to-electric charge conversion is carried out by photodiodes of the optoelectronic conversion elements.

Cumulative capacitors 46, which accumulate the charges generated in the optoelectronic conversion layer, and pixel portions 50, which are provided with TFTs 48 for read-out of the charges accumulated in the cumulative capacitors 46, are numerously provided in a matrix form on the TFT active matrix substrate 44 (the optoelectronic conversion layer corresponding with each of the pixel portions 50 is schematically shown as an optoelectronic conversion portion 52 in FIG. 3). The charges that are generated in the optoelectronic conversion layer in accordance with irradiation of the radiation X onto the electronic cassette 20 are accumulated in the individual cumulative capacitors 46 of the pixel portions 50. Thus, the image information carried by the radiation X irradiated onto the electronic cassette 20 is converted to electric charge information and retained in the radiation detector 36.

Plural gate lines 54 and plural data lines 56 are provided in the TFT active matrix substrate 44. The gate lines 54 extend in a certain direction (a column direction) and are for turning the TFTs 48 of the pixel portions 50 on and off. The data lines 56 are provided in a direction crossing the gate lines 54 (a row direction) and are for reading out the accumulated charges from the cumulative capacitors 46 via the TFTs 48 that have been turned on. The respective gate lines 54 are connected to a gate line driver 58, and the respective data lines 56 are connected to a signal processing section 60. When charges are accumulated in the cumulative capacitors 46 of the respective pixel portions 50, the TFTs 48 of the pixel portions 50 are turned on sequentially, column by column, by signals provided through the gate lines 54 from the gate line driver 58. The charges accumulated in the cumulative capacitors 46 of the pixel portions 50 for which the TFTs 48 have been turned on are transferred through the data lines 56 as charge signals and inputted to the signal processing section 60. Thus, the charges accumulated in the cumulative capacitors 46 of the respective pixel portions 50 are sequentially read out in column units.

Figure 4:
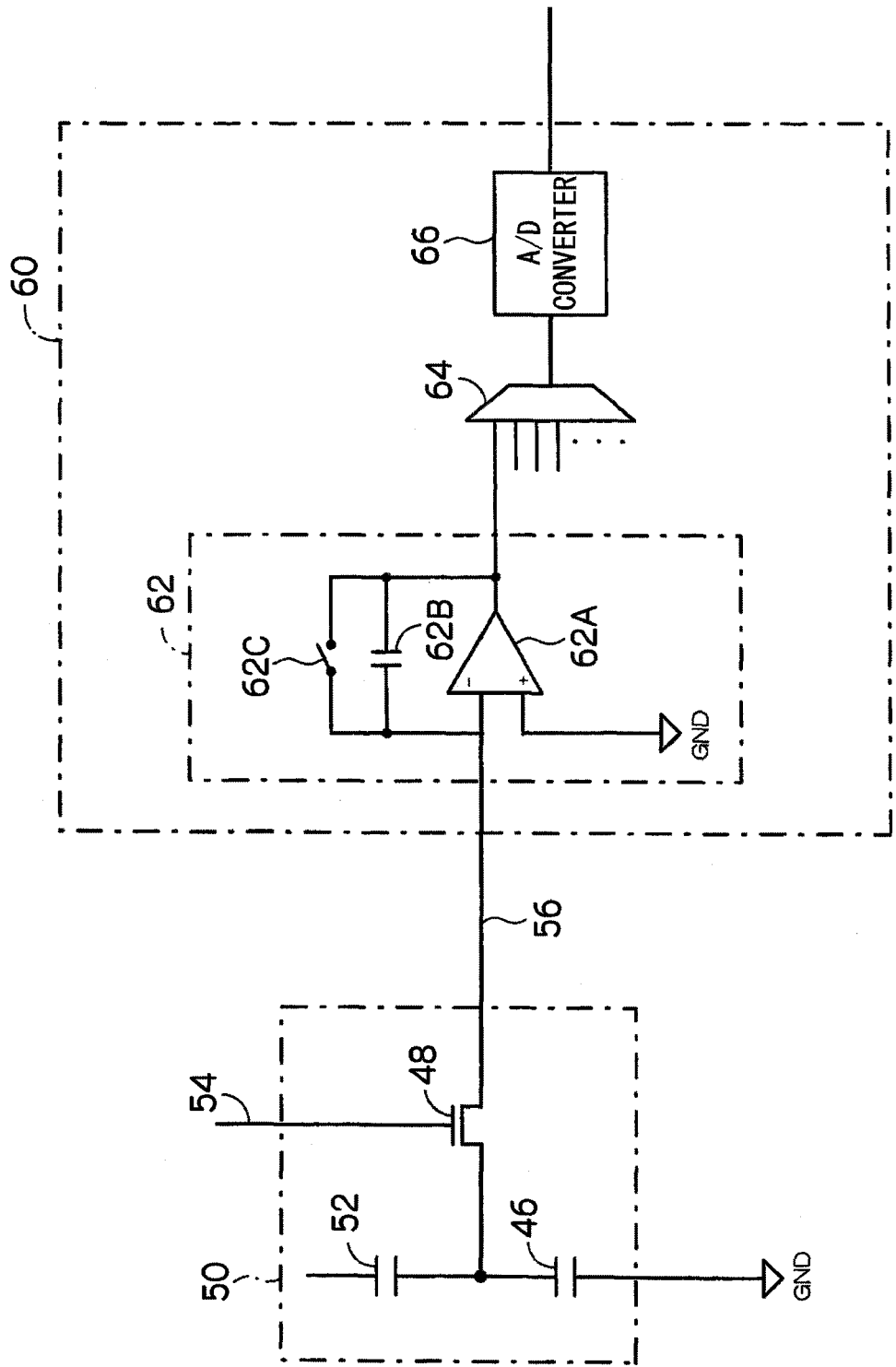
FIG. 4 is an equivalent circuit diagram concerning a single-pixel portion of a radiation detector relating to the first exemplary embodiment.

FIG. 4 shows an equivalent circuit diagram concerning a single-pixel portion of the radiation detector 36 relating to the present exemplary embodiment.

As shown in FIG. 4, the source of the TFT 48 is connected to the data line 56, and the data line 56 is connected to the signal processing section 60. The drain of the TFT 48 is connected to the cumulative capacitor 46 and the optoelectronic conversion portion 52, and the gate of the TFT 48 is connected to the gate line 54.

The signal processing section 60 is provided with a sample and hold circuit 62 for each data line 56. The charge signals transferred through the data lines 56 are retained at the respective sample and hold circuits 62. The sample and hold circuit 62 is structured to include an op amp 62A and a capacitor 62B, and converts charge signals to analog voltages. The sample and hold circuit 62 is further provided with a switch 62C, which serves as a reset circuit that shorts together the two electrodes of the capacitor 62B and discharges charge accumulated in the capacitor 62B.

A multiplexer 64 and an A/D converter 66 are connected, in this order, to the output side of the sample and hold circuit 62. The charge signals retained by the respective sample and hold circuits are converted to analog voltages, sequentially (serially) inputted into the multiplexers 64, and converted to digital image data by the A/D converters 66.

A line memory 68 is connected to the signal processing section 60 (see FIG. 3), and the image information outputted from the A/D converters 66 of the signal processing section 60 is sequentially stored in the line memory 68. The line memory 68 has a storage capacity capable of storing a predetermined number of lines of image information representing a radiographic image. Each time reading of charges for one line is carried out, the image information corresponding to the one line that is read out is sequentially stored in the line memory 68.

The line memory 68 is connected with a cassette control section 70 that controls overall operations of the electronic cassette 20. The cassette control section 70 is realized by a microcomputer and is connected to an optical communications control section 72. The optical communications control section 72 is connected to the connection terminal 20A, and implements control of transfers of various kinds of information between the optical communications control section 72 and external equipment that is connected via the connection terminal 20A. Thus, the cassette control section 70 is capable of transmitting and receiving various kinds of information to and from the external equipment via the optical communications control section 72.

The electronic cassette 20 is further provided with a display driver 74, which performs display control of the display 26. The cassette control section 70 is connected to the display driver 74. The cassette control section 70 reads out image information stored in the line memory 68 and causes a radiographic image represented by the image information to be displayed at the display 26.

The electronic cassette 20 is also provided with a power supply section 76. The aforementioned various circuits and elements (the gate line driver 58, the signal processing section 60, the line memory 68, the optical communications control section 72, a microcomputer that functions as the cassette control section 70, and the like) are driven by power supplied from the power supply section 76. The power supply section 76 incorporates a battery (a rechargeable secondary cell) so as not to impede portability of the electronic cassette 20, and provides power to the various circuits and elements from the charged battery.

The console 24 is structured to serve as a server computer. The console 24 is provided with a display 80, which displays control menus, imaged radiographic images and the like, and a control panel 82, which is structured to include plural keys and at which various kinds of information and control instructions are inputted (see also FIG. 1).

The console 24 relating to the present exemplary embodiment is provided with: a CPU 84 that administers overall operations of the device; a ROM 86 at which various programs, including a control program, and the like are stored in advance; a RAM 88 that temporarily stores various kinds of data; an HDD (hard disc drive) 90 that stores and retains various kinds of data; a display driver 92 that controls displays of various kinds of information at the display 80; a control input detection section 94 that detects control conditions at the control panel 82; a communications interface (I/F) section 96 that is connected to the connection terminal 24A and carries out exchanges of various kinds of information, such as exposure conditions, information on the state of the radiation irradiation device 18 and the like, with the radiation irradiation device 18 via the connection terminal 24A and the communications cable 41; and an optical communications control section 98 that is connected to the connection terminal 24B and carries out exchanges of various kinds of information, such as image information and the like, with the electronic cassette 20 via the connection terminal 24B and the communications cable 42.

The ROM 86 relating to the present exemplary embodiment stores a plurality of categories of related information, associating subject information representing subjects of imaging with detection region information representing detection regions of the radiation detector 36, with sizes corresponding to the subjects of imaging.

In the present exemplary embodiment, four kinds of information are employed as the above-mentioned subject information: information representing (a) imaging location(s) (below referred to as imaging location information); information representing gender (below referred to as gender information); information representing race (below referred to as ethnicity information); and information representing age (below referred to as age information). However, this is not limiting. For example, any one, two or three kinds of information from the imaging location information, the gender information, the ethnicity information and the age information may be employed as the subject information. Alternatively, in addition to the above-mentioned imaging location information, gender information, ethnicity information and age information, information representing body weight, information representing height and the like may also be employed as the subject information. Any kind of information may be used provided the information is useful for deriving a general size of the subject of imaging.

The CPU 84, the ROM 86, the RAM 88, the HDD 90, the display driver 92, the control input detection section 94, the communications I/F section 96 and the optical communications control section 98 are connected to one another by a system bus. Thus, the CPU 84 may implement access to the ROM 86, the RAM 88 and the HDD 90, and may implement each of control of display of various kinds of information at the display 80 via the display driver 92, acquisition of details of states of control by users from the control panel 82 via the control input detection section 94, control of exchanges of various kinds of information with the radiation irradiation device 18 via the communications I/F section 96, and control of exchanges of various kinds of information with the electronic cassette 20 via the optical communications control section 98.

The radiation irradiation device 18 is provided with a radiation source 100 that outputs the radiation X, a communications I/F section 102, and a radiation source control section 104. The communications I/F section 102 exchanges various kinds of information, such as exposure conditions, information on the state of the radiation irradiation device 18 and the like, with the console 24. The radiation source control section 104 controls the radiation source 100 on the basis of the received exposure conditions. The radiation source control section 104 is realized by a microcomputer, stores the received exposure conditions, and causes the radiation X to be irradiated from the radiation source 100 in accordance with the exposure conditions.

In the imaging system 10 relating to the present exemplary embodiment, the cassette control section 70 of the electronic cassette 20 periodically (in the imaging system 10 of the present exemplary embodiment, once each ten times of imaging) detects defective pixels in a detection-capable region of the radiation detector 36, and sends position information representing positions of the defective pixels in the detection-capable region to the console 24. In response, radiographic imaging assistance processing that assists imaging of radiographic images using the electronic cassettes 20 is executed at the console. The cassette control section 70, for example, reads out the charge accumulated in each of the pixel portions 50 of the radiation detector 36 without irradiation with radiation from the radiation irradiating device 18, and detects defective pixels based on whether or not the amount of charge read out is within a normal range for a state in which radiation is not irradiated.

Figure 6:
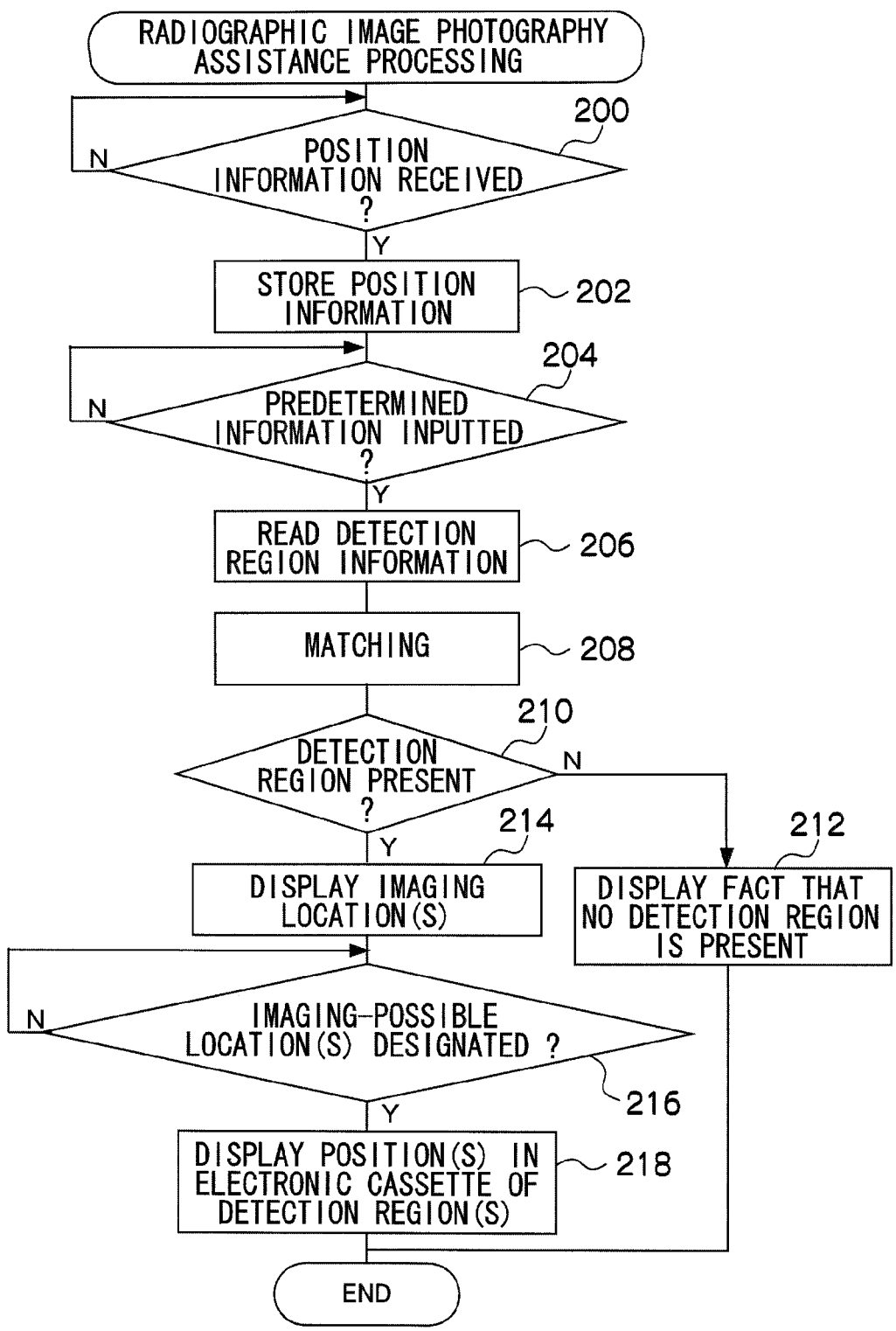
FIG. 6 is a flowchart illustrating a flow of processing of a radiographic imaging assistance processing program relating to the first exemplary embodiment.

Now, a processing routine at the console 24 when the above-mentioned radiographic imaging assistance processing is executed will be described with reference to FIG. 6. FIG. 6 is a flowchart illustrating a flow of processing of a radiographic imaging assistance processing program that is executed by the CPU 84 of the electronic cassette 20 at this time. This program is stored in a predetermined region of the ROM 86 beforehand.

In step 200 of FIG. 6, the processing waits to receive position information that is sent from the electronic cassette 20. Then, in step 202, the position information received in step 200 is stored in the HDD 90 as defective pixel information. If defective pixel information has previously been stored in the HDD 90, it is updated to the new defective pixel information.

Then, in step 204, the processing waits for input of patient name information, which represents the name of the patient 14, and subject information through the control panel 82. When the patient name information and subject information are inputted, as illustrated by the example in FIG. 7, the patient name represented by the patient name information, the ethnicity represented by ethnicity information included in the subject information, the gender represented by gender information included in the subject information, the age represented by age information included in the subject information, and the imaging location(s) represented by imaging location information included in the subject information are displayed at the display 80.

Figure 8A:
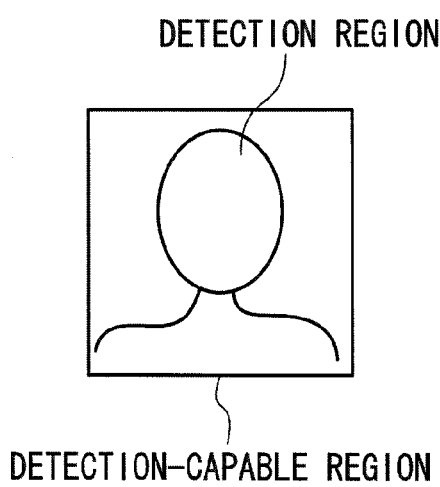
FIG. 8A is detection region information illustrating radiation detection regions in a case of imaging the upper body of an average-sized 15-year-old Japanese female.
Figure 8B:
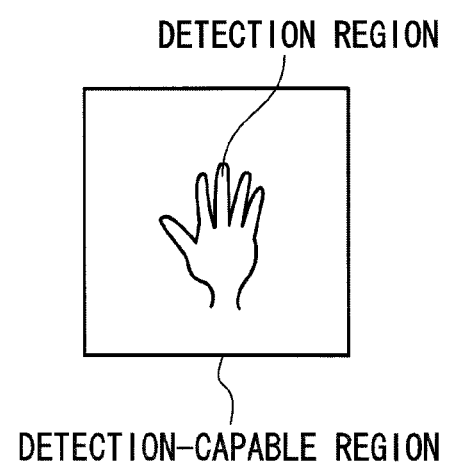
FIG. 8B is detection region information illustrating radiation detection regions in a case of imaging a hand of an average-sized 15-year-old Japanese female.

Next, in step 206, detection region information that is associated with the subject information inputted in step 204 is read from the ROM 86. FIG. 8A and FIG. 8B schematically illustrate examples of detection region information relating to the present exemplary embodiment. FIG. 8A is detection region information illustrating radiation detection regions in a case of imaging the upper body of an average-sized 15-year-old Japanese female, and FIG. 8B is detection region information illustrating radiation detection regions in a case of imaging a hand of an average-sized 15-year-old Japanese female.

Then, in step 208, the defective pixel information stored in the HDD 90 and the detection region information read out in step 206 are matched up.

Figure 5:
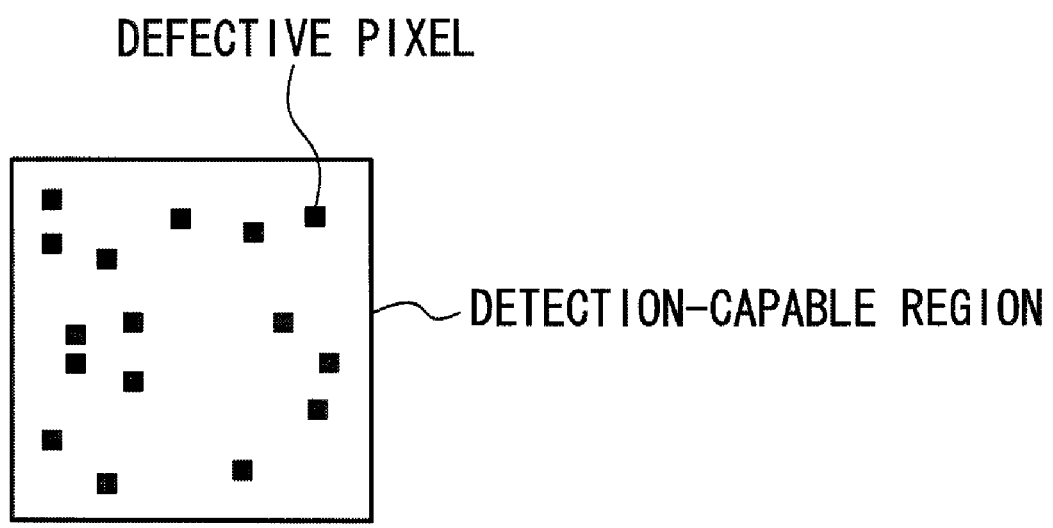
FIG. 5 is a schematic diagram illustrating an example of positions of defective pixels in a detection-capable region of the radiation detector relating to the first exemplary embodiment.
Figure 9A:
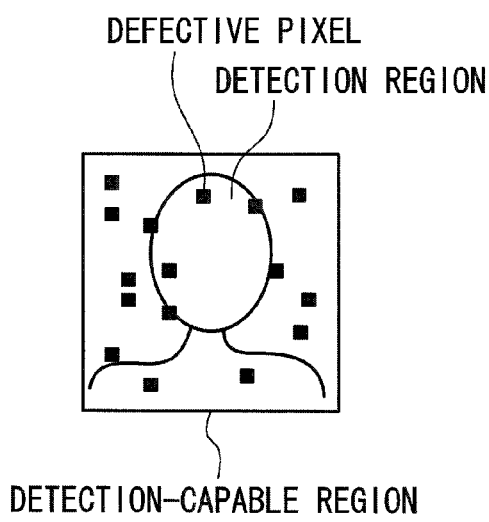
FIG. 9A is a schematic view of an example of a case in which the defective pixel information illustrated in FIG. 5 is matched up with the detection region information illustrated in FIG. 8A.
Figure 9B:
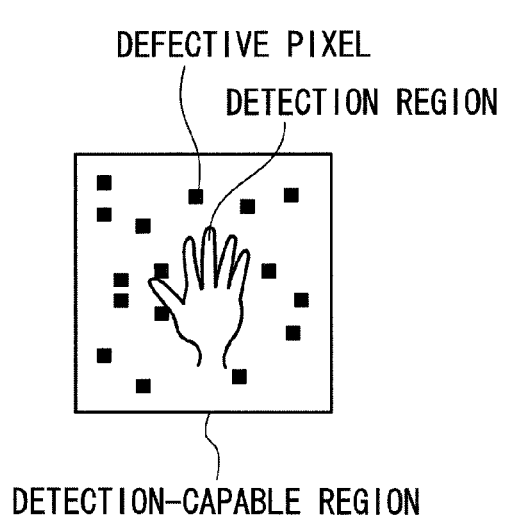
FIG. 9B is a schematic view of an example of a case in which the defective pixel information illustrated in FIG. 5 is matched up with the detection region information illustrated in FIG. 8B.

FIG. 9A and FIG. 9B schematically illustrate examples of cases in which the defective pixel information illustrated in FIG. 5 is matched up with the detection region information illustrated in FIG. 8A and FIG. 8B. As shown in FIG. 9A, if the effective pixel information shown in FIG. 5 is matched up with the defective pixel information shown in FIG. 8A, the defective pixels represented by the defective pixel information overlap with the detection regions represented by the detection region information. Therefore, radiation X transmitted through the patient 14 and irradiated at the radiation detector 36 would be affected by the defective pixels in detection. In contrast, as shown in FIG. 9B, if the effective pixel information shown in FIG. 5 is matched up with the defective pixel information shown in FIG. 8B, the defective pixels represented by the defective pixel information do not overlap with the detection regions represented by the detection region information. Therefore, radiation X transmitted through the patient 14 and irradiated at the radiation detector 36 would be detected without being affected by the defective pixels.

In step 210, it is judged whether or not there is a detection region that is capable of detecting radiation X transmitted through the patient 14 and irradiated at the radiation detector 36 without being affected by defective pixels. If this judgment is negative, the processing advances to step 212, the fact that there is not a detection region capable of detecting the radiation X without being affected by defective pixels is displayed at the display 80, and the present radiographic imaging assistance processing program ends.

On the other hand, if the judgment of step 210 is positive, the processing advances to step 214, in which imaging location information corresponding to detection region information that represents detection regions in which detection, without the radiation X being affected by defective pixels, is possible and imaging location information corresponding to detection region information that represents detection regions in which detection, without the radiation X being affected by defective pixels, is not possible are distinguishably displayed at the display 80.

Figure 10:
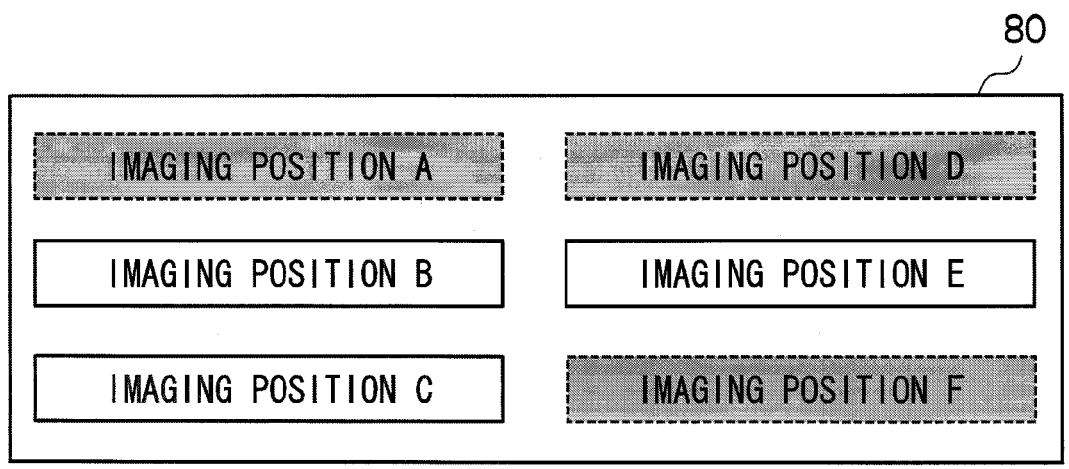
FIG. 10 is a view illustrating an example of a display screen that displays: imaging location information corresponding to detection region information that represents detection regions that are capable of detecting radiation without being affected by defective pixels; and imaging location information corresponding to detection region information that represents detection regions that are not capable of detecting radiation without being affected by the defective pixels.

FIG. 10 illustrates an example of a display screen that displays the imaging location information corresponding to the detection region information that represents detection regions that may detect the radiation without being affected by defective pixels and the imaging location information corresponding to the detection region information that represents detection regions that may not detect the radiation without being affected by defective pixels. As is shown in FIG. 10, of the imaging locations represented by the imaging location information included in the subject information that was inputted in step 204 (in this case, imaging locations A, B, C, D and E), only the imaging locations represented by imaging location information that corresponds to the detection region information representing the detection regions that may be detected without the radiation X being affected by defective pixels are highlighted (in this case, imaging locations B, C and E).

In step 216, designation of the imaging location information that corresponds to the detection region information representing the detection regions that may be detected without the defective pixels affecting the radiation X is carried out via the control panel 82. Then, in step 218, positions in the electronic cassette 20 of the detection regions represented by the detection region information that corresponds to the imaging location information designated in step 216 are ascertainably displayed at the display 80, and the present radiographic imaging assistance processing program ends.

By the processing of step 218, the detection regions represented by the detection region information that corresponds to the imaging location information designated in step 216 are displayed at the display 80, for example, as shown in FIG. 9B. Thus, a technician may easily see how the imaging location(s) may be satisfactorily disposed relative to the electronic cassette 20. Hence, the imaging locations may be arranged to avoid the positions of the defective pixels in the electronic cassette 20. Thus, repetitions of imaging due to defective pixels may be avoided.

As has been described in detail hereabove, at the console 24 relating to the present exemplary embodiment: position information is acquired that represents positions of defective pixels in the electronic cassette 20, which carries out imaging by detecting radiation X that has passed through the patient 14, generating image information representing the radiographic image in accordance with the detected radiation amounts and storing the image information in the line memory 68; on the basis of detection region information representing detection regions with sizes depending on the patient 14 and of the acquired position information, it is judged whether or not there are detection regions which may be detected without the radiation X that has passed through the detection object patient 14 being affected by the defective pixels; and control is performed to display the judgment results at the display 80. Hence, repetitions of imaging due to defective pixels may be avoided.

Further, at the console 24 relating to the present exemplary embodiment, when it is judged that there are detection regions which may be detected without the radiation X that has passed through the detection object patient 14 being affected by the defective pixels, control is performed so as to ascertainably display the positions in the electronic cassette 20 of the detection regions. When it is judged that there are no detection regions that may be detected without the radiation X that has passed through the detection object patient 14 and been irradiated at the radiation detector 36 being affected by the defective pixels, control is performed so as to display the fact that no detection region is present that may be detected without the radiation X being affected by the defective pixels. Hence, the imaging locations may be arranged to avoid the positions in the electronic cassette 20 of the defective pixels. Thus, excellent quality radiographic images may be obtained without redoing the imaging.

Further yet, at the console 24 relating to the present exemplary embodiment, the control panel 82 at which subject information is inputted is provided. The CPU 84 judges whether or not there is a detection region which may be detected, without radiation that has passed through the patient 14 and been irradiated being affected by defective pixels, on the basis of detection region information corresponding to the subject information inputted by the control panel 82 and the position information sent from the electronic cassette 20. Thus, the size of a detection region may be easily estimated.

[Second Exemplary Embodiment]

Explanation will now be given of a second exemplary embodiment. A feature of the second exemplary embodiment is that defective pixels in the detection-capable region of the radiation detectors 36 are periodically detected and transmitted to a server computer provided at an external data center, and in the server computer judgment is made as to whether or not the influence from defective pixels is at an acceptable level to permit capture of radiographic images.

Figure 11:
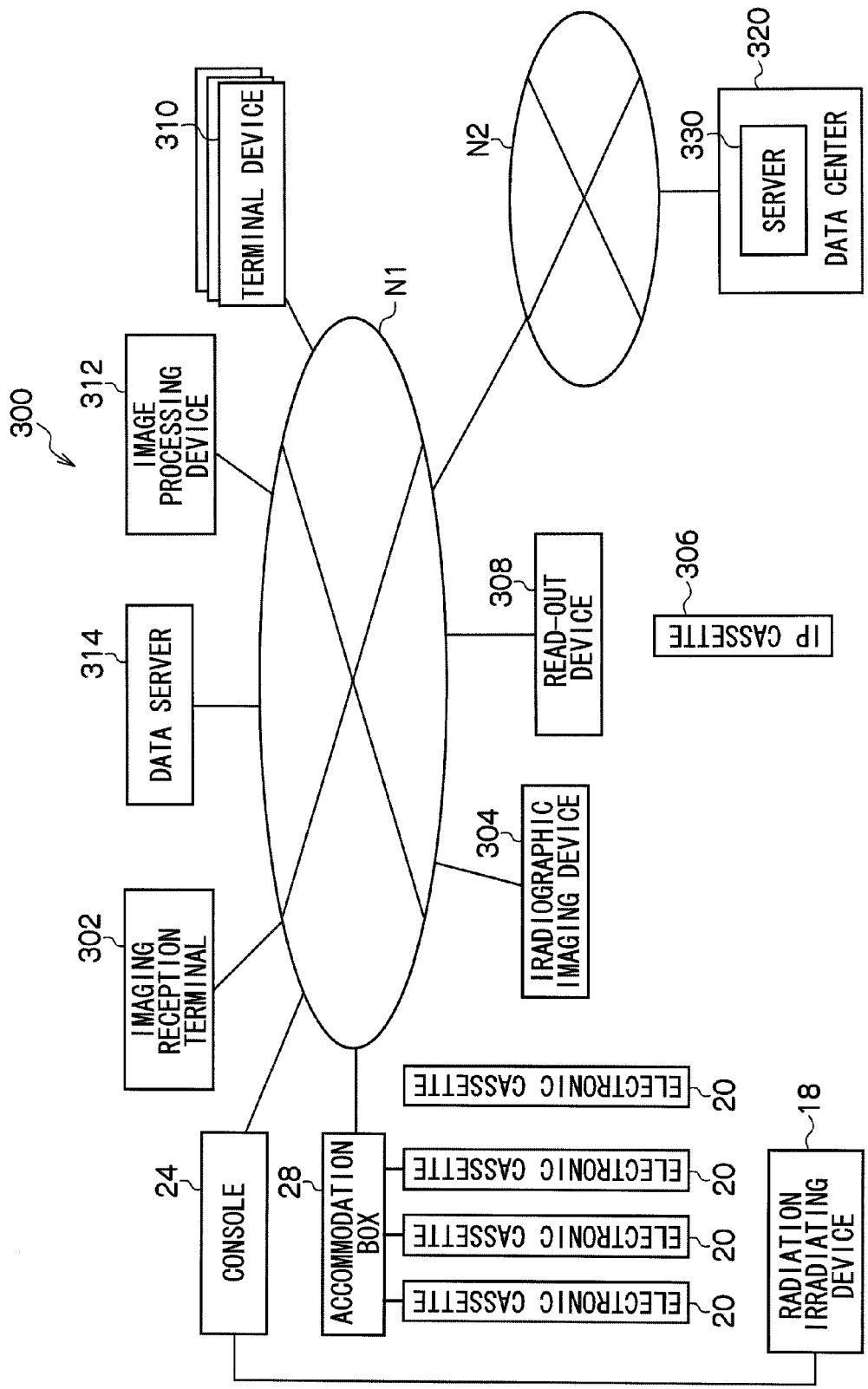
FIG. 11 is a block diagram illustrating the overall configuration of a Hospital Information System according to a second exemplary embodiment.

FIG. 11 is a block diagram illustrating an overall schematic configuration of a Hospital Information System (HIS) 300 of a hospital overall, including a radiographic imaging system 10.

The radiographic imaging system 10 according to the second exemplary embodiment configures a portion of the HIS 300, and, in addition to the console 24, the plural electronic cassettes 20, the accommodation box (cradle) 28 and the radiation irradiating device 18 explained in the above first exemplary embodiment, the HIS 300 is also equipped with an imaging reception terminal 302, a fixed radiographic imaging device 304 housing a built-in radiation detector, an IP cassette 306 with built-in image plate (IP), and a read-out device 308 that reads out a radiographic image from the image plate built into the IP cassette 306.

The console 24, the accommodation box 28, the imaging reception terminal 302, the fixed radiographic imaging device 304 and the read-out device 308 are connected together by a hospital internal network N1 so as to be able to communicate.

There are also plural terminal devices 310, an image processing device 312, and a data server 314 connected to the hospital internal network N1.

The terminal devices 310 are for a doctor or radiographer to input and/or view consultation information and facility appointments, and radiographic imaging requests (imaging appointments) are also made through the terminal devices 310. Each of the terminal devices 310 are configured by a personal computer with display.

The image processing device 312 is configured by a server computer, and various image processing programs are stored in the image processing device 312, for performing image processing appropriate for interpreting radiographic images and performing image processing for identifying lesions. The image processing device 312 performs various types of image processing on image information representing a radiographic image obtained by image capture.

The data server 314 stores image information representing radiographic images obtained by image capture and image information that has been image processed by the image processing device 312.

The imaging reception terminal 302 is provided at the entrance to the imaging room where radiographic images are captured, and reception processing is performed with the imaging receiver terminal 302 when a doctor or radiographer is capturing radiographic images.

The accommodation box 28 according to the second exemplary embodiment connects the electronic cassettes 20 accommodated therein to the hospital internal network N1 so as enable communication. In FIG. 11 the electronic cassettes 20 accommodated in the accommodation box 28 are connected to the accommodation box 28 by wires. It should be noted that the electronic cassettes 20 may be wireless communication enabled, and wireless communication performed with the console 24 and the hospital internal network N1.

The HIS 300 is also connected to an external network N2, such as the internet, through a networking device such as a router, enabling communication to be performed via the external network N2 with a server computer (referred to below as "server") 330 provided in a data center 320.

Figure 12:
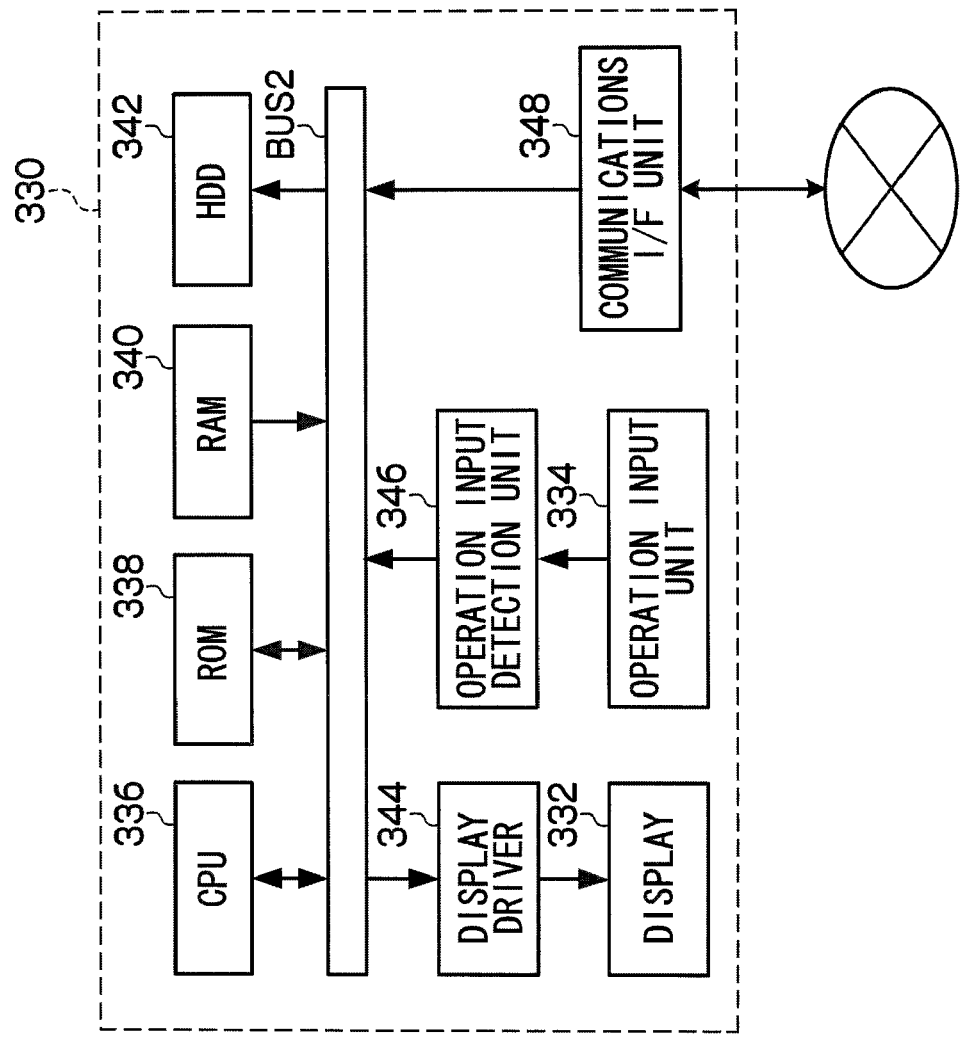
FIG. 12 is a block diagram illustrating the configuration of a server according to the second exemplary embodiment.

FIG. 12 illustrates a detailed configuration of a server 330 according to the present exemplary embodiment.

The server 330 is equipped with a display 332 that displays an operation menu, messages etc., and an operation input unit 334, such as a keyboard and pointer device etc., through which various operation instructions are input by a user.

The server 330 is also equipped with: a CPU 336 that controls the operation of the devices overall; a ROM 338, serving as a recording medium, on which various programs and the like, including a control program, are stored in advance; a RAM 340 on which various data is temporarily stored; an HDD 342 on which various data, including installed software, is stored and held; a display driver 344 that controls display of various information on the display 332; an operation input detection unit 346 that detects the operational state of the operation input unit 334; and a communications I/F unit 348 for performing communication with an external network N2.

In the present exemplary embodiment, related information, associating subject information representing investigation subjects with detection region information representing detection regions of the radiation detector 36, with sizes corresponding to the investigation subjects, is stored on the HDD 342. In the present exemplary embodiment, imaging location information representing imaging location is appropriately employed as the above subject information, and detection region information representing standard detection regions according to the imaging location is stored on the HDD 342 for each of the imaging locations. Note that the above subject information is not limited to imaging location information representing the imaging location, and, for example, detection region information representing standard detection regions may be stored on the HDD 342 for each of imaging location, gender, ethnicity, or age as imaging location information, gender information, ethnicity information, or age information in a similar manner to that of the first exemplary embodiment. In addition one, two or three types of information may be employed from imaging location information, gender information, ethnicity information, and age information. As well as the above mentioned imaging location information, gender information, ethnicity information, and age information, information representing body weight, information representing body height and the like are employable as the subject information, and any general information that is useful in deriving the size of the subject may be employed.

The CPU 336, the ROM 338, the RAM 340, the HDD 342, the display driver 344, the operation input detection unit 346, and the communications I/F unit 348 are mutually connected to each other via a system BUS 2. Consequently the CPU 336 accesses the ROM 338, the RAM 340, and the HDD 342, controls the display of various information on the display 332 via the display driver 344, and controls transmission and receipt of data to and from the radiation irradiating device 18 via the communications I/F unit 348. The CPU 336 ascertains the operational state of a user toward the operation input unit 334 through the operation input detection unit 346.

In the electronic cassettes 20 of the present exemplary embodiment, defective pixels in the detection-capable region of the radiation detector 36 are periodically detected, and position information representing the positions of such defective pixels in the detection-capable region are transmitted to the console 24, under the control of the cassette control section 70.

The console 24 transmits the position information representing the position of the defective pixels of each of the electronic cassettes 20 to the server 330 via the hospital internal network N1 and the external network N2.

When in receipt of the position information representing the position of the defective pixels of each of the electronic cassettes 20 from the console 24, the server 330 stores the received position information as defective pixel data in the HDD 342. The server 330 periodically executes replacement timing judgment processing, based on the defective pixel data stored in the HDD 342, judging the replacement timing of each of the electronic cassettes 20.

Figure 13:
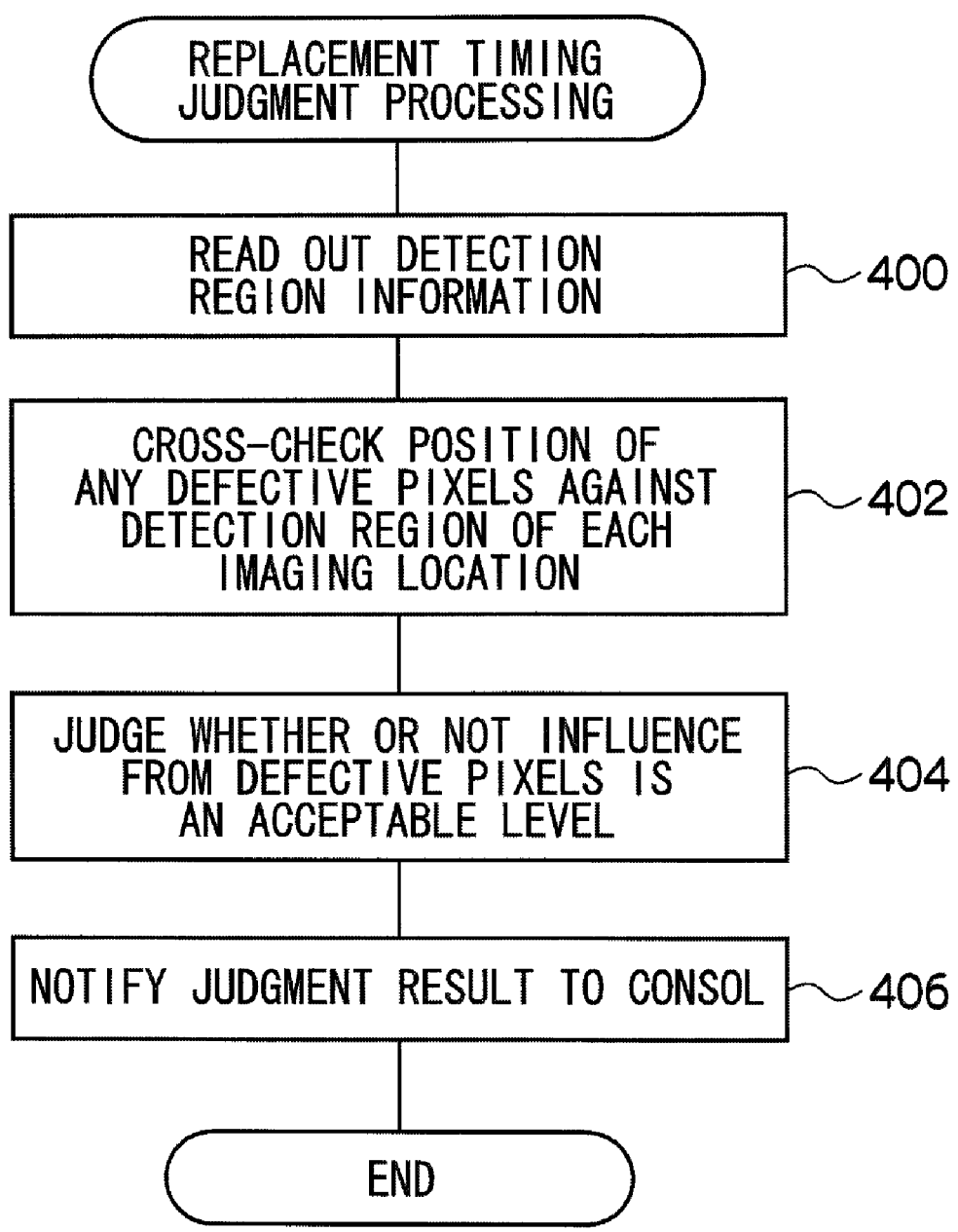
FIG. 13 is a flow chart illustrating the process flow of a replacement timing judgment processing program according to the second exemplary embodiment.

Explanation will now be made of a processing routine in the console 24 when executing the above replacement timing judgment processing, with reference to FIG. 13. FIG. 13 is a flow chart illustrating the process flow in the replacement timing judgment processing program executed by the CPU 336 of the server 330 on such occasions, this program being stored in advance in a specific region of the HDD 342.

At step 400 in FIG. 13, detection region information representing standard detection regions for each imaging location are read out from the HDD 342.

At the next step 402 the position of the defective pixels of each of the respective electronic cassettes 20, represented by the defective pixel data stored in the HDD 90, is crosschecked against the respective standard detection regions for each imaging location represented by the detection region information read out in step 400 above.

At the next step 404, judgment is made, for each of the electronic cassettes 20, as to whether or not the influence from defective pixels in the standard detection regions of each of the imaging locations represented in the detection region information is at an acceptable level to permit capture of radiographic images.

Figure 14:
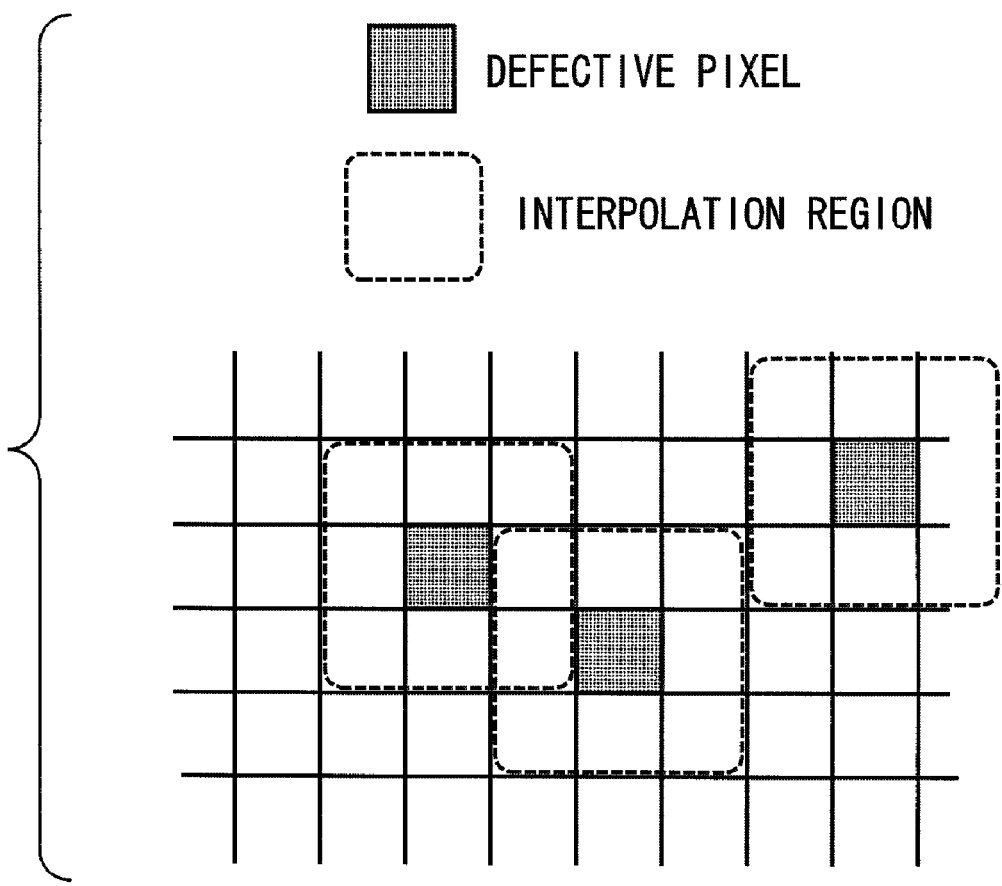
FIG. 14 is a plan view illustrating an example of the disposal of defective pixels for a judgment that the influence from the defective pixels is within an acceptable level.
Figure 15:
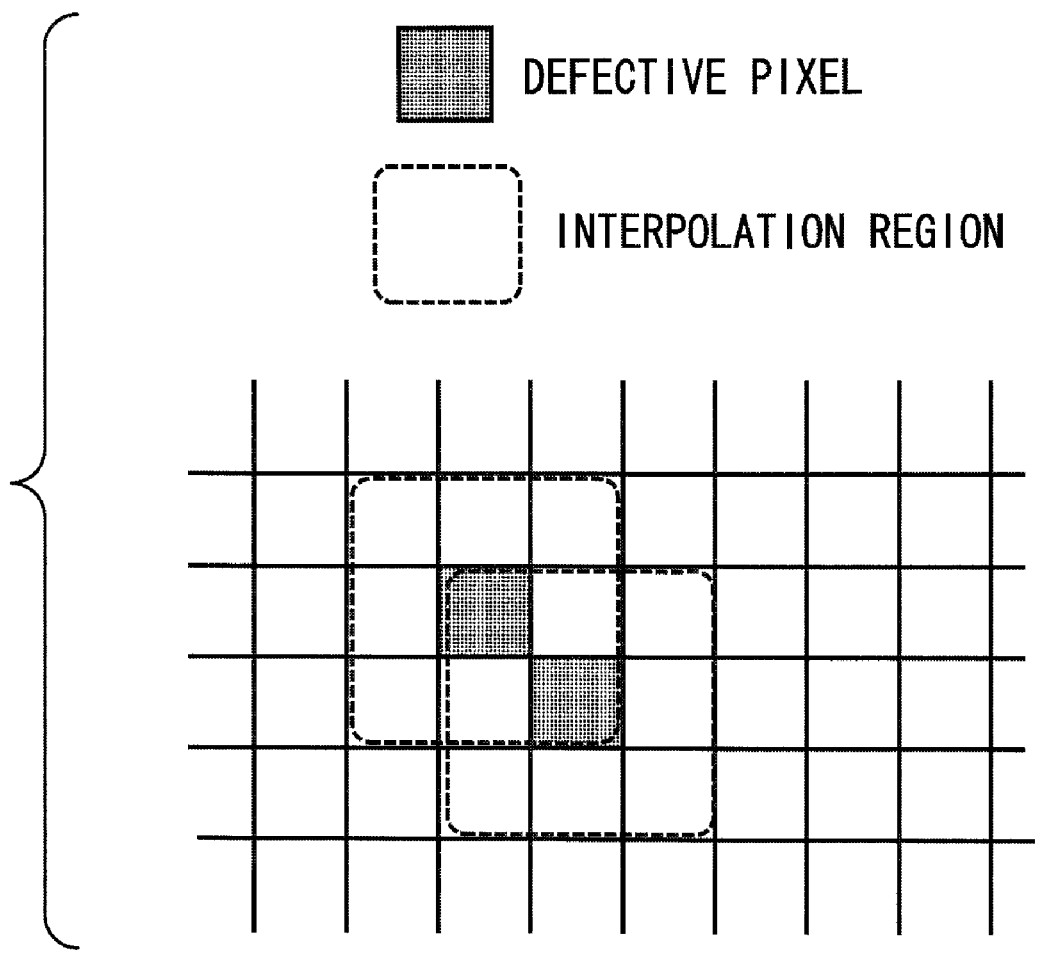
FIG. 15 is a plan view illustrating an example of the disposal of defective pixels for a judgment that the influence from the defective pixels is outside an acceptable level.

For example, when the average value of data of other pixels in a predetermined interpolation region surrounding such a defective pixel is used for interpolation of the data of the defective pixel, in the present exemplary embodiment, when there are defective pixels present in the detection region, if there are other defective pixels present in the interpolation region surrounding such a defective pixel judgment of not an acceptable level is made. In this manner, even if there are plural defective pixels present in the detection region, judgment is made of an acceptable level as long as the defective pixels are not in the interpolation regions of each other, as shown in FIG. 14, however if the defective pixels are present in the interpolation regions of each other, as shown in FIG. 15, then judgment is made of not an acceptable level.

Explanation has been given here of a case where the average value of data of other pixels in the interpolation region surrounding a defective pixel is used to interpolate the data of the defective pixel, however there is no limitation thereto. For example, a weighted sum of data of other pixels in the interpolation region surrounding a defective pixel may be used as the data of the defective pixel, and various other interpolation methods can be employed.

At the next step 406, the judgment result data representing the judgment result of each of the imaging locations of each of the electronic cassettes 20 is notified to the console 24 via the external network N2 and the hospital internal network N1, and processing is ended.

The console 24 displays, for each of the imaging locations of each of the electronic cassettes 20, whether or not there is an acceptable level permitting capture of radiographic images. Judgment can thereby be made as to which of the electronic cassettes 20 is appropriate for imaging according to the imaging location.

The electronic cassettes 20 with which the influence from the defective pixels is within an acceptable level according to the imaging location on the patient 14 may be displayed. Or, when, for example, imaging location information, gender information, ethnicity information, or age information is employed as the above subject information, in a similar manner to in the first exemplary embodiment, the electronic cassettes 20 where the influence from the defective pixels is within an acceptable level according to the imaging location, gender, ethnicity, or age of the patient 14 may be displayed.

When there are none of the electronic cassettes 20 where the influence from the defective pixels is within an acceptable level, the console 24 may display a message prompting imaging with the fixed radiographic imaging device 304, or may display a message prompting imaging with the IP cassette 306.

As explained in detail above, control is made in the server 330 according to the present exemplary embodiment such that: X-ray radiation that has passed through the patient 14 is detected; image information is generated representing a radiographic image according to the amount of radiation detected; position information representing the position of defective pixels of the electronic cassette 20 for imaging is acquired by storing image information in the line memory 68; judgment is made as to whether or not the influence from the defective pixels in the detection region represented by the detection region information is at an acceptable level permitting imaging of a radiographic image, based on the detection region information, representing the detection region of size according to the imaging location of the patient 14, and the acquired position information; and the judgment result is notified to the console 24. Consequently, re-imaging due to defective pixels can be prevented.

Hereabove, the present invention has been described using the above first and second exemplary embodiments, but the technical scope of the present invention is not to be limited to the scope described in the above exemplary embodiment. Numerous modifications and improvements may be applied to the above first and second exemplary embodiments within a scope not departing from the spirit of the invention, and modes to which modifications and/or improvements are applied are to be encompassed by the technical scope of the invention.

Furthermore, the above first and second exemplary embodiments are not limiting to the inventions recited in the claims, and not all of the combination of characteristics described in the above exemplary embodiment are necessarily required for a resolution of the invention. Inventions with various stages of the above exemplary embodiment are to be included, and various inventions may be derived by combinations of the disclosed plurality of structural elements in accordance with circumstances. Even if some structural element is removed from the totality of structural elements illustrated in the above exemplary embodiment, as long as the effects are obtained, a structure from which this some structural element has been removed may be derived to serve as the invention.

For example, in the above first exemplary embodiment, an example of a case in which the radiographic imaging assistance processing is executed at the console 24 has been described. However, the present invention is not to be limited thus; the radiographic imaging assistance processing may be executed at the electronic cassette 20. In such a case, if, for example, a touch panel display is constituted by superposing a transparent touch panel over the display 26, various kinds of information are displayed at the display screen of the display 26 and the user inputs desired information and instructions by touching the touch panel. The radiographic imaging assistance processing program described above is executed by the cassette control section 70. Thus, the same operations and effects may be obtained at the electronic cassette 20 as in the case in which the radiographic imaging assistance processing is executed at the console 24.

In the above first exemplary embodiment, explanation has been given of an exemplary mode for a case where judgment as to whether or not there is a detection-capable region present not affected by defective pixels by whether or not the defective pixels represented by the defective pixel data are superimposed on the detection region represented by the detection region information, however the present invention is not limited thereto. As in the second exemplary embodiment, judgment may be made as to whether or not the influence from any defective pixels in the detection region is at an acceptable level permitting imaging of a radiographic image.

In the above second exemplary embodiment, explanation has been given of an exemplary mode for a case in which judgment is made as to whether or not the influence from any defective pixels in the detection region is at an acceptable level permitting imaging of a radiographic image, however the present invention is not limited thereto. As in the first exemplary embodiment, judgment may be made as to whether or not there is a detection-capable region present not affected by defective pixels.

In the above first and second exemplary embodiments, a warning may be displayed when the influence from defective pixels of the electronic cassette 20 exceeds the acceptable level for all of the imaging locations or specific imaging location(s). By so doing, since the deterioration of the electronic cassette 20 is known by a doctor 12 or radiographer this thereby acts as motivation for maintenance of the electronic cassette 20.

In the above first and second exemplary embodiment, the degree of deterioration of the electronic cassette 20 can be associated with data representing the imaging location that is to be subjected to imaging, and stored in an internal memory of the electronic cassette 20 or in the HDD 90 of the console 24. By so doing, control can be made of whether appropriate imaging has been made for the imaging location.

Image information representing a captured radiographic image, defective pixel data of the electronic cassette 20 that has capture the radiographic image, and data representing whether or not there is an acceptable level, may be associated as with each other as deterioration data related to deterioration, and stored. Such associating and storing includes storing deterioration data in a header, footer, or tag of the image information itself, and also associating deterioration data with the image information and storing. Control can thereby be achieved of which defective pixels are present in the electronic cassette 20 the radiographic image has been captured on, and traceability improved.

Further, in the above first and second exemplary embodiments, an example has been described of a case in which defective pixels in the detection-capable region of the radiation detector 36 are detected by the electronic cassette 20 and the position information representing positions of these defective pixels is sent to the console 24 periodically. However, the present invention is not limited thus. For example, the electronic cassette 20 may detect the defective pixels and send the position information to the console 24 in response to instructions from the console 24. Accordingly, timings of detection of defective pixels in the radiation detector 36 and transmission of position information to the console by the electronic cassette 20 may be suitably varied.

In the above first exemplary embodiment, an example has been described of a case in which the information representing whether or not there are detection regions that may be detected without the radiation X being affected by the defective pixels is displayed at the display 80. However, the present invention is not limited thus. For example, the information representing whether or not there are detection regions that may be detected without the radiation X being affected by the defective pixels may be sent to the electronic cassette 20 and displayed at the display 26 of the electronic cassette 20.

In the above first exemplary embodiment, an example has been described of a case in which positions in the electronic cassette 20 of the detection regions represented by the detection region information are ascertainably displayed at the display 80. However, the present invention is not limited thus. For example, the positions in the electronic cassette 20 of the detection regions represented by the detection region information may be displayed at the display 26.

In the second exemplary embodiment explanation has been given of a case where judgment is made that the influence from defective pixels is an acceptable level when there are no other defective pixels in an interpolation region of a given defective pixel in the detection region, however there is no limitation thereto. For example, judgment of an acceptable level may be made when there are a specific number of individual defective pixels in the detection region, or fewer. This specific number may be variable by input to the operation input unit 334 by a user. In the second exemplary embodiment, the number of interpolation regions present where there are other defective pixels in the interpolation region of the defective pixels may also be counted, and judgment of an acceptable level made when the number of counted interpolation regions is a specific number or fewer. The specific number may also be variable by input to the operation input unit 334 by a user.

In the second exemplary embodiment, explanation has been given of a case where judgment result data is notified to the console 24, however there is no limitation thereto. For example, notification may be made to the terminal device 310 of a person monitoring the electronic cassettes 20.

In the second exemplary embodiment, explanation has been given of a case in which the judgment result data is notified, however there is no limitation thereto. For example, the judgment result and data representing all of the electronic cassettes 20 that have been judged not to have an acceptable level for a specific imaging location may be notified, or data representing all of the electronic cassettes 20 that have been judged not to have an acceptable level for a specific imaging location may be notified. By so doing, replacement of deteriorated electronic cassettes 20 can be prompted by notifying electronic cassettes 20 that have deteriorated to a level outside of the acceptable level.

Moreover, the constitution of the imaging system 10 described in the above first and second exemplary embodiments (see FIG. 1 to FIG. 4) is an example and obviously may be altered in accordance with circumstances within a scope not departing from the spirit of the present invention.

Furthermore, the processing flow of the radiographic imaging assistance processing program described in the above exemplary embodiment (see FIG. 6) is an example and obviously unnecessary steps may be removed, new steps may be added and the processing sequence may be rearranged within a scope not departing from the spirit of the present invention.

A radiographic imaging assistance device of a first aspect of the present invention includes: an acquisition component that acquires position information representing positions of defective pixels of an imaging device, the imaging device being plurally provided with pixels comprising detection elements which detect radiation that has passed through a subject of imaging, and the imaging device carrying out imaging by generating image information which represents a radiographic image in accordance with radiation amounts detected by the detection elements and storing the image information in a pre-specified storage region; a judgment component that, on the basis of detection region information, which represents a detection region with a size corresponding to the subject of imaging, and the position information acquired by the acquisition component, judges whether or not an influence from the defective pixels in a detection region that is represented by the detection region information is within an acceptable level that accepts imaging a radiographic image; and a control component that performs control such that information based on a judgment result judged by the judgment component is displayed at a display component or notified to an external device.

According to the radiographic imaging assistance device of the first aspect, the imaging device is plurally provided with the pixels constituted with the detection elements that detect radiation which has passed through a subject of imaging, and carries out imaging by generating the image information representing the radiographic image in accordance with the radiation amounts detected by the detection elements and storing the image information in the pre-specified storage region. The position information representing positions of defective pixels of the imaging device is acquired by the acquisition component.

In the present exemplary embodiment, the judgment component judges whether or not an influence from the defective pixels in a detection region that is represented by the detection region information is within an acceptable level that accepts imaging a radiographic image, on the basis of the detection region information representing a detection region with a size corresponding to the subject of imaging and the position information acquired by the acquisition component.

Then, in the present invention, control is performed by the control component such that information based on the judgment result judged by the judgment component is displayed at the display component or notified to an external device.

Thus, according to the radiographic imaging assistance device of the present invention, it is judged whether or not the influence from the defective pixels in the detection region is within the acceptable level that accepts imaging a radiographic image, on the basis of the detection region with a size corresponding to the subject of imaging and the positions of the defective pixels of the imaging device, the information based on the judgment results are displayed or notified, and thus repetitions of imaging that are caused by defective pixels may be avoided.

In the radiographic imaging assistance device of the first aspect of the present invention, the judgment component may judge that there is the acceptable level when there is a detection-capable region present where the irradiated radiation that has passed through the subject of imaging is not affected by defective pixels. Thereby, the imaging can be carried out in the detection region that is not affected by the defective pixels. Accordingly, repetitions of imaging that are caused by defective pixels may be avoided.

In the radiographic imaging assistance device of the first aspect of the present invention, the judgment component may judge that there is the acceptable level when there is no other defective pixel in an interpolation region for interpolating data of a defective pixel in the detection region. Thereby, when data of a defective pixel in the radiographic image is interpolated by data of other pixel within a predetermined interpolation region surrounding the defective pixel, it is judged that there is the acceptable level if the data of the defective pixel can be corrected without being affected by the other defective pixel. Accordingly, repetitions of imaging that are caused by defective pixels may be avoided.

In the radiographic imaging assistance device of the first aspect of the present invention, wherein the judgment component may judge that there is the acceptable level when a number of defective pixels present in the detection region is a specific number or fewer. Thereby, even when there are defective pixels in the detection region, if the number of the defective pixels is small and thus the influence is a little, imaging of the radiographic image can be carried out.

In the radiographic imaging assistance device of the first aspect of the present invention, in a case in which it is judged by the judgment component that the influence from the defective pixels is within the acceptable level, the control component may perform control such that a position of the detection region at the imaging device is ascertainably displayed, and in a case in which it is judged that the influence from the defective pixels is not within the acceptable level, the control component may performs control such that the fact that the detection region is not present is displayed. Therefore, the subject of imaging may be arranged to avoid positions of the defective pixels at the imaging device, and thus excellent quality radiographic images may be obtained without redoing the imaging.

The radiographic imaging assistance device of the first aspect may include an input component that inputs information representing at least one of an age, imaging location, body weight, height and gender of the subject of imaging and wherein the judgment component may judge whether or not the influence from the defective pixels in the detection region that is represented by the detection region information is within the acceptable level that accepts imaging a radiographic image on the basis of detection region information corresponding to the information inputted by the input component and the position information acquired by the acquisition component. Thus, the size of the detection region may be easily estimated.

A radiographic imaging device of a second aspect of the present invention includes: an imaging component that is plurally provided with pixels that are constituted with detection elements which detect radiation which has passed through a subject of imaging, and that carries out imaging by generating image information which represents a radiographic image in accordance with radiation amounts detected by the detection elements and storing the image information in a pre-specified storage region; an acquisition component that acquires position information representing positions of defective pixels of the imaging component; a judgment component that, on the basis of detection region information, which represents a detection region with a size corresponding to the subject of imaging, and the position information acquired by the acquisition component, judges whether or not an influence from the defective pixels in a detection region that is represented by the detection region information is within an acceptable level that accepts imaging a radiographic image; and a control component that performs control such that information based on a judgment result judged by the judgment component is displayed at a display component or notified to an external device.

Thus, the radiographic imaging device of the present invention operates similarly to the radiographic imaging assistance device of the present invention and, similarly to the radiographic imaging assistance device, repetitions of imaging that are caused by defective pixels may be avoided.

In the radiographic imaging device of the second aspect, the judgment component may judge that there is the acceptable level when there is a detection-capable region present where the irradiated radiation that has passed through the subject of imaging is not affected by defective pixels. Thereby, the imaging can be carried out in the detection region that is not affected by the defective pixels. Accordingly, repetitions of imaging that are caused by defective pixels may be avoided.

In the radiographic imaging device of the second aspect, the judgment component may judge that there is the acceptable level when there is no other defective pixel in an interpolation region for interpolating data of a defective pixel in the detection region. Thereby, when data of a defective pixel in the radiographic image is interpolated by data of other pixel within a predetermined interpolation region surrounding the defective pixel, it is judged that there is the acceptable level if the data of the defective pixel can be corrected without being affected by the other defective pixel. Accordingly, repetitions of imaging that are caused by defective pixels may be avoided.

In the radiographic imaging device of the second aspect, the judgment component may judge that there is the acceptable level when a number of individual defective pixels present in the detection region is a specific number or fewer. Thereby, even when there are defective pixels in the detection region, if the number of the defective pixels is small and thus the influence is a little, imaging of the radiographic image can be carried out.

In the radiographic imaging device of the second aspect, in a case in which it is judged by the judgment component that the influence from the defective pixels is within the acceptable level, the control component performs control such that a position of the detection region is ascertainably displayed, and in a case in which it is judged the influence from the defective pixels is not within the acceptable level, the control component may perform control such that the fact that the detection region is not present is displayed. Therefore, the subject of imaging may be arranged to avoid positions of the defective pixels at the radiographic imaging device, and thus excellent quality radiographic images may be obtained without redoing the imaging.

The radiographic imaging device of the second aspect may include an input component that inputs information representing at least one of an age, imaging location, body weight, height and gender of the subject of imaging, wherein the judgment component judges whether or not the influence from the defective pixels in the detection region that is represented by the detection region information is within the acceptable level that accepts imaging a radiographic image on the basis of detection region information corresponding to the information inputted by the input component and the position information acquired by the acquisition component. Thus, the size of the detection region may be easily estimated.

A third aspect of the present invention is a storage medium readable by a computer. The storage medium stores a program of instructions executable by the computer to perform a function for assisting radiographic imaging. The function includes: (a) acquiring position information representing positions of defective pixels of an imaging device, the imaging device being plurally provided with pixels comprising detection elements which detect radiation that has passed through a subject of imaging, and the imaging device carrying out imaging by generating image information which represents a radiographic image in accordance with radiation amounts detected by the detection elements and storing the image information in a pre-specified storage region; (b) on the basis of detection region information, which represents a detection region with a size corresponding to the subject of imaging, and the position information acquired in (a), judging whether or not an influence from the defective pixels in a detection region that is represented by the detection region information is within an acceptable level that accepts imaging a radiographic image; and (c) performing control such that information based on a judgment result judged in (b) is displayed at a display component or notified to an external device.

Thus, according to the third aspect, operations are similar to the invention of the first aspect and, similarly to the first aspect, repetitions of imaging that are caused by defective pixels may be avoided.

The program of the third aspect may be a program for causing a computer to function as the acquisition component, judgment component and control component of the radiographic imaging assistance device of the first aspect.

Thus, according to the program of the third aspect, operations are similar to the radiographic imaging assistance device of the first aspect, and the same effects may be obtained as with the radiographic imaging assistance device.

According to the present invention there is an effect in that repetitions of imaging that are caused by defective pixels may be avoided.

What is claimed is:
1. A radiographic imaging assistance device comprising:
an acquisition component that acquires position information representing positions of defective pixels of an imaging device, the imaging device being plurally provided with pixels comprising detection elements which detect radiation that has passed through a subject of imaging, and the imaging device carrying out imaging by generating image information which represents a radiographic image in accordance with radiation amounts detected by the detection elements and storing the image information in a pre-specified storage region;

a judgment component that, on the basis of detection region information, which represents a detection region with a size corresponding to the subject of imaging, and the position information acquired by the acquisition component, judges whether or not an influence from the defective pixels in a detection region that is represented by the detection region information is within an acceptable level that accepts imaging a radiographic image; and a control component that performs control such that information based on a judgment result judged by the judgment component is displayed at a display component or notified to an external device.

2. The radiographic imaging assistance device of claim 1, wherein the judgment component judges that there is the acceptable level when there is a detection-capable region present where the irradiated radiation that has passed through the subject of imaging is not affected by defective pixels.

3. The radiographic imaging assistance device of claim 1, wherein the judgment component judges that there is the acceptable level when there is no other defective pixel in an interpolation region for interpolating data of a defective pixel in the detection region.

4. The radiographic imaging assistance device of claim 1, wherein the judgment component judges that there is the acceptable level when a number of defective pixels present in the detection region is a specific number or fewer.

5. The radiographic imaging assistance device of claim 1 wherein, in a case in which it is judged by the judgment component that the influence from the defective pixels is within the acceptable level, the control component performs control such that a position of the detection region at the imaging device is ascertainably displayed, and in a case in which it is judged that the influence from the defective pixels is not within the acceptable level, the control component performs control such that the fact that the detection region is not present is displayed.

6. The radiographic imaging assistance device of claim 1, further comprising an input component that inputs information representing at least one of an age, imaging location, body weight, height and gender of the subject of imaging,
   wherein the judgment component judges whether or not the influence from the defective pixels in the detection region that is represented by the detection region information is within the acceptable level that accepts imaging a radiographic image on the basis of detection region information corresponding to the information inputted by the input component and the position information acquired by the acquisition component.

7. The radiographic imaging assistance device of claim 1, further comprising a receiver component that receives instruction of the acceptable level.

8. A radiographic imaging device comprising:
   an imaging component that is plurally provided with pixels comprising detection elements which detect radiation which has passed through a subject of imaging, and that carries out imaging by generating image information which represents a radiographic image in accordance with radiation amounts detected by the detection elements and storing the image information in a pre-specified storage region;
   an acquisition component that acquires position information representing positions of defective pixels of the imaging component;

a judgment component that, on the basis of detection region information, which represents a detection region with a size corresponding to the subject of imaging, and the position information acquired by the acquisition component, judges whether or not an influence from the defective pixels in a detection region that is represented by the detection region information is within an acceptable level that accepts imaging a radiographic image; and a control component that performs control such that information based on a judgment result judged by the judgment component is displayed at a display component or notified to an external device.

9. The radiographic imaging device of claim 8, wherein the judgment component judges that there is the acceptable level when there is a detection-capable region present where the irradiated radiation that has passed through the subject of imaging is not affected by defective pixels.

10. The radiographic imaging device of claim 8, wherein the judgment component judges that there is the acceptable level when there is no other defective pixel in an interpolation region for interpolating data of a defective pixel in the detection region.

11. The radiographic imaging device of claim 8, wherein the judgment component judges that there is the acceptable level when a number of individual defective pixels present in the detection region is a specific number or fewer.

12. The radiographic imaging device of claim 8 wherein, in a case in which it is judged by the judgment component that the influence from the defective pixels is within the acceptable level, the control component performs control such that a position of the detection region is ascertainably displayed, and in a case in which it is judged that the influence from the defective pixels is not within the acceptable level, the control component performs control such that the fact that the detection region is not present is displayed.

13. The radiographic imaging device of claim 8, further comprising an input component that inputs information representing at least one of an age, imaging location, body weight, height and gender of the subject of imaging,
   wherein the judgment component judges whether or not the influence from the defective pixels in the detection region that is represented by the detection region information is within the acceptable level that accepts imaging a radiographic image on the basis of detection region information corresponding to the information inputted by the input component and the position information acquired by the acquisition component.

14. A storage medium readable by a computer, the storage medium storing a program of instructions executable by the computer to perform a function for assisting radiographic imaging, the function comprising:
   (a) acquiring position information representing positions of defective pixels of an imaging device, the imaging device being plurally provided with pixels comprising detection elements which detect radiation that has passed through a subject of imaging, and the imaging device carrying out imaging by generating image information which represents a radiographic image in accordance with radiation amounts detected by the detection elements and storing the image information in a pre-specified storage region;
   (b) on the basis of detection region information, which represents a detection region with a size corresponding to the subject of imaging, and the position information acquired in (a), judging whether or not an influence from the defective pixels in a detection region that is represented by the detection region information is within an acceptable level that accepts imaging a radiographic image; and (c) performing control such that information based on a judgment result judged in (b) is displayed at a display component or notified to an external device.

15. The storage medium of claim 14 wherein, in a case in which it is judged in (b) that the influence from the defective pixels is within the acceptable level, (c) includes performing control such that a position of the detection region at the imaging device is ascertainably displayed, and in a case in which it is judged that the influence from the defective pixels is not within the acceptable level, (c) includes performing control such that the fact that the detection region is not present is displayed.

16. The storage medium of claim 14, further comprising (d) inputting information representing at least one of an age, imaging location, body weight, height and gender of the subject of imaging, wherein (b) includes judging whether or not the influence from the defective pixels in the detection region that is represented by the detection region information is within the acceptable level that accepts imaging a radiographic image on the basis of detection region information corresponding to the information inputted in (d) and the position information acquired in (a).

* * * * *